US012059512B2

(12) United States Patent
Burd

(10) Patent No.: US 12,059,512 B2
(45) Date of Patent: Aug. 13, 2024

(54) CABIN ISOLATION ASSEMBLIES

(71) Applicant: B/E Aerospace, Inc., Winston Salem, NC (US)

(72) Inventor: Peter Burd, Burry Port (GB)

(73) Assignee: B/E AEROSPACE, INC., Winston Salem, NC (US)

( * ) Notice: Subject to any disclaimer, the term of this patent is extended or adjusted under 35 U.S.C. 154(b) by 547 days.

(21) Appl. No.: 17/327,459

(22) Filed: May 21, 2021

(65) Prior Publication Data
US 2021/0361817 A1 Nov. 25, 2021

Related U.S. Application Data

(60) Provisional application No. 63/028,690, filed on May 22, 2020.

(51) Int. Cl.
| A61L 9/20 | (2006.01) |
| A61L 9/14 | (2006.01) |
| B64C 1/14 | (2006.01) |
| B64D 11/00 | (2006.01) |
| B64D 13/06 | (2006.01) |

(52) U.S. Cl.
CPC ............... *A61L 9/20* (2013.01); *A61L 9/145* (2013.01); *B64C 1/1407* (2013.01); *B64D 11/00* (2013.01); *B64D 13/06* (2013.01); *A61L 2209/12* (2013.01); *A61L 2209/14* (2013.01); *A61L 2209/21* (2013.01); *A61L 2209/22* (2013.01); *B64D 2011/0046* (2013.01); *B64D 2011/0069* (2013.01); *B64D 2013/0651* (2013.01); *B64D 2013/0688* (2013.01)

(58) Field of Classification Search
CPC ........ A61L 9/20; A61L 9/145; A61L 2209/12; A61L 2209/14; A61L 2209/21; A61L 2209/22; B64C 1/1407; B64D 11/00; B64D 13/06; B64D 2011/0046; B64D 2011/0069; B64D 2013/0651; B64D 2013/0688; A61G 2220/10
See application file for complete search history.

(56) References Cited

U.S. PATENT DOCUMENTS

| 2002/0144601 A1* | 10/2002 | Palestro | A61L 9/20 95/273 |
| 2008/0250559 A1* | 10/2008 | Janboecke | B64D 11/00 5/2.1 |
| 2010/0304658 A1* | 12/2010 | Grcevic | B60P 3/14 454/187 |
| 2021/0322589 A1* | 10/2021 | Matter | A61L 2/26 |

FOREIGN PATENT DOCUMENTS

| CN | 110667854 A * | 1/2020 | |
| WO | WO-2005052459 A2 * | 6/2005 | B60H 1/00371 |

* cited by examiner

Primary Examiner — Edelmira Bosques
Assistant Examiner — Michael James Giordano
(74) Attorney, Agent, or Firm — SNELL & WILMER L.L.P.

(57) ABSTRACT

An isolation section assembly includes a section housing defining an interior space. The section housing includes a door with access to the interior space. The isolation section assembly includes an enclosure abutting the door. The airlock enclosure defines an interior airlock space. The interior airlock space is configured and adapted to be at a negative pressure relative to a cabin area. An air recirculation system in fluid communication with at least one of the interior space of the section housing or the interior airlock space.

13 Claims, 5 Drawing Sheets

CABIN ISOLATION ASSEMBLIES

CROSS-REFERENCE TO RELATED APPLICATION

This application claims priority to and the benefit of U.S. Provisional application No. 63/028,690, filed May 22, 2020, the entire contents of which are herein incorporated by reference in their entirety.

BACKGROUND

1. Field

The present disclosure relates generally to passenger cabins, and more particularly to cabin sections for environmentally isolating some passengers from other passengers.

2. Description of Related Art

The COVID-19 outbreak has raised the demands of cleanliness and prevention of cross-contamination of viruses between passengers in common-carrier cabins, such as those of aircrafts. Customers, ground personnel and cabin crew may wear protective gear but possible cross-contamination between passengers may still occur, especially if a passenger or crew member falls ill during the flight.

There is an ongoing need for improved systems and methods to reduce cross-contamination between passengers in common areas such as cabin seating areas. This disclosure provides a solution for this need.

SUMMARY

An isolation section assembly includes a section housing defining an interior space. The section housing includes at least one door with access to the interior space. The isolation section assembly includes an enclosure abutting the door. The airlock enclosure defines an interior airlock space. The interior airlock space is configured and adapted to be at a negative pressure relative to a cabin area. An air recirculation system in fluid communication with at least one of the interior space of the section housing or the interior airlock space.

The section housing can include a UV illumination system positioned within the interior space configured and adapted to disinfect the interior space. The air recirculation system can include an inlet conduit and a return conduit, and an environmental conditioner therebetween. The environmental conditioner can include a carbon filter, an ozone scrubber, a UVC light and/or a chemical sanitizer. The return conduit can be in fluid communication with an $O_2$ source to receive $O_2$ therefrom. The return conduit can fluidly connect an outlet of the environmental conditioner and the interior space of the section housing. The interior space of the section housing can include at least one bunk bed, at least one reclining chair, or both. The interior space of the section housing can include a waste stowage system. The interior space of the section housing can include a medical supply storage area.

In some embodiments, the door described above is a first door. The isolation section assembly can include a second door with access to the interior space and a second airlock enclosure abutting the second door. The second airlock enclosure can define a second interior airlock space. The second interior airlock space can be configured and adapted to be at a negative pressure relative to a cabin area. The second door can opposite from the first door across the interior space. The second door can be mounted on a common wall with the first door.

The isolation section assembly can include a communications and electrical interface input operatively connected to the section housing. The isolation section assembly can include at least one connection point operatively connected to the section housing. The at least one connection point can be configured and adapted to couple to at least one existing monument connection point in an aircraft cabin.

In accordance with another aspect, a method for retrofitting an aircraft with an isolation section assembly system includes mounting a section housing to existing cabin monument connection points in a passenger cabin. The method includes coupling an airlock enclosure to a door of the section housing. The method includes fluidly coupling an air recirculation system to at least one of an existing cabin air exhaust or an existing $O_2$ source.

The method can include electrically connecting a communications and electrical interface input on the section housing to at least one of an existing vehicle communications system or an existing aircraft power source.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
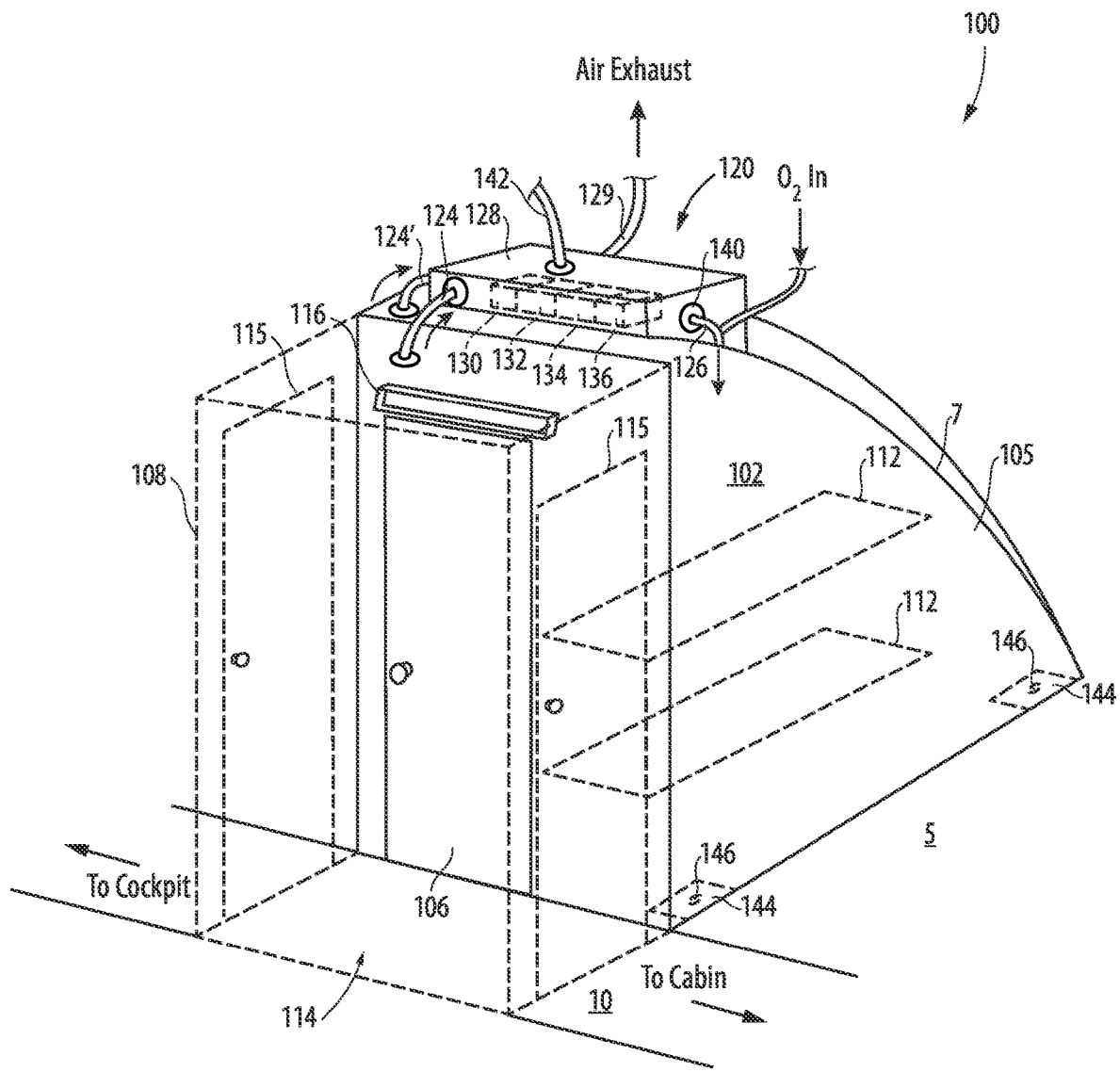
FIG. 1 is a schematic perspective view of an embodiment of an isolation section assembly constructed in accordance with the present disclosure, showing the section housing.

Reference will now be made to the drawings wherein like reference numerals identify similar structural features or aspects of the subject disclosure. For purposes of explanation and illustration, and not limitation, a view of an embodiment of an isolation section assembly, e.g. "pod," in accordance with the disclosure is shown in FIG. 1 and is designated generally by reference character 100. Other embodiments of systems in accordance with the disclosure, or aspects thereof, are provided in FIGS. 2-6, as will be described. Embodiments of systems and methods described herein can be used to house and transport one or more individuals who may have taken ill during a flight or other type of travel by keeping them environmentally isolated. Embodiments of systems and methods described herein may also allow for the ill passengers to be attended to by medical staff without risking cross-contamination for other passengers and crew. The pod could serve to isolate passengers taken ill during the transport or can transport individuals taken ill on holiday, as part of a standard passenger service.

Figure 2:
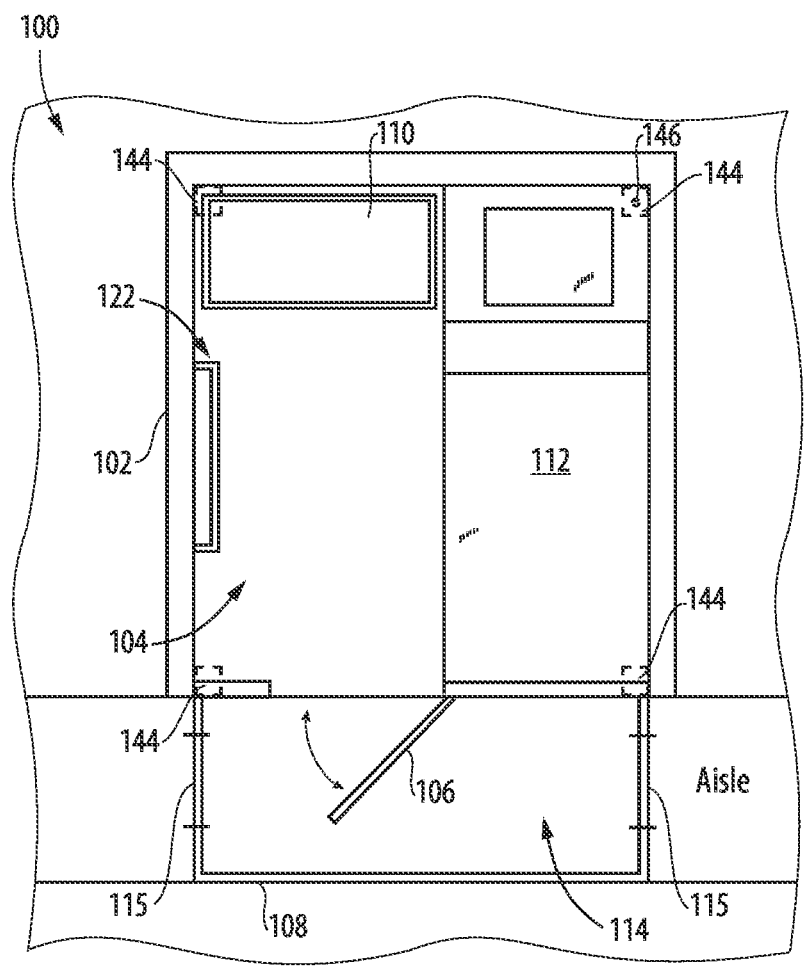
FIG. 2 is a schematic plan view of the isolation section assembly of FIG. 1, showing the interior space of the section housing.

As shown in FIGS. 1 and 2, an isolation section assembly 100 is configured and adapted to replace or repurpose an in situ the Forward Crew Rest Compartment (FCRC) on long hall aircraft or any suitable location on other forms of mass transit transport. The isolation section assembly 100, or "pod," includes a section housing 102 defining an interior space 104 isolated from a cabin area 10, e.g. an aircraft cabin. The isolation section assembly 100 can take the form of a smaller compartment within the cabin area 10, or a section equal in scale to the remainder of the cabin area, but isolated therefrom. The side walls 105 of the section housing 102 extend from a cabin floor 5 and connect to a top wall 109 of section housing 102 to form a complete, isolated enclosure from the rest of the cabin area 10. The section housing 102 includes a door 106 with access to the interior space 104. The section housing 102 can be constructed using known techniques and known materials used for other cabin structures. This will enable a more efficient certification process and reduced point of embodiment time (e.g., its planned introduction). Those skilled in the art will appreciate that the isolation section assembly 100 can be used in cabins of other non-aviation forms of transport (e.g. train, ships etc.).

With reference now to FIGS. 1 and 2, the isolation section assembly 100 includes an airlock enclosure 108 abutting the door 106. The interior space 104 of the section housing 102 includes a medical supply storage area 110, which can be equipped with oxygen inputs or tanks, monitors, ventilators and other suitable medical equipment as the customer dictates. The interior space 104 of the section housing 102 includes beds 112, e.g. bunk beds. A bunk lift system could be an option to allow 2 or 3 bunks to be placed one above the other if required. The section 102 is configured and adapted to provide isolation for sick patients while also accommodating access for an attendant. The section housing 102 includes a FAR-UV illumination system 122 positioned within the interior space 104 configured and adapted to disinfect the interior space 104.

With continued reference to FIGS. 1 and 2, the airlock enclosure 108 defines an interior airlock space 114. The interior airlock space 114 is configured and adapted to be at a negative pressure relative to a cabin area 10 to inhibit the escape of potentially contaminated air from interior space 104 of the section housing 102. Interior airlock space 114 includes a constant FAR-UVC* illumination system 116 for sterilization to afford entry and egress for medical attendants if present. The airlock enclosure 108 can be made from a glass fiber honeycomb material configured and adapted to block UV. Illumination system 116 is mounted to an exterior surface 118 of section housing 102 and is configured to direct the UV light toward the interior airlock space 114. Airlock enclosure 108 includes forward and aft access doors 115 to allow passage from the cabin area 10 through to the cockpit and/or into the airlock space 114 while the door 106 into interior space 104 is closed. In isolation section assembly 100 the airlock enclosure 108 is placed in the aisle, but as the assembly 100 is located adjacent to the cockpit door, generally no passengers would need to transit through the airlock enclosure 108, only cabin crew or the pilot/co-pilot requiring a comfort break.

As shown in FIGS. 1 and 2, an air recirculation system 120 is in fluid communication with the interior space 104 of the section housing 102 and the interior airlock space 114. The air recirculation system 120 includes an inlet conduit 124 and a return conduit 126. An environmental conditioner 128 is positioned between the inlet conduit 124 and return conduit 126. The air recirculation system 120 and environmental conditioner 128 takes air from the interior airlock space 114 via inlet conduit 124 or the interior space 104 of the section housing 102 via second return conduit 124' and transfers it through sanitizers/filters and thoroughly scrubs the air through a combination of UVC light, Chemical Sanitizers and Carbon filters. The scrubbed air can be exhausted to the vent system or can be recirculated back into the interior space 104 of the section housing 102. The environmental conditioner 128 includes at least one of a carbon filter 130, an ozone scrubber 132, a UVC light 134 or a chemical sanitizer 136. The return conduit 126 is in fluid communication with an $O_2$ source 138 to receive $O_2$ therefrom to increase the oxygen level in the space and or a personal oxygen mask or hood. The return conduit 126 fluidly connects an outlet 140 of the environmental conditioner 128 and the interior space 104 of the section housing 102.

With continued reference to FIGS. 1 and 2, the isolation section assembly 100 includes a communications and electrical interface input 142 operatively connected to the section housing 102 via recirculation system 120. The isolation section assembly 100 includes connection points 144 operatively connected to the section housing 102. The connection points 144 are configured and adapted to couple to existing monument connection points 146 in aircraft cabin area 10. This allows for the section housing 102 to replace existing in-service galley monuments as a bolt-out, bolt-in option. Those skilled in the art will readily appreciate that the isolation assembly 100 can be customized as needed to fit a given aircraft layout and/or requirements of a given airline customer. Additionally, because the isolation section assembly 100 is configured to attach to existing connection points in the cabin area, post-pandemic, the aircraft fitted with the pods can be re-converted to standard passenger carrying and catering configurations.

Figure 3:
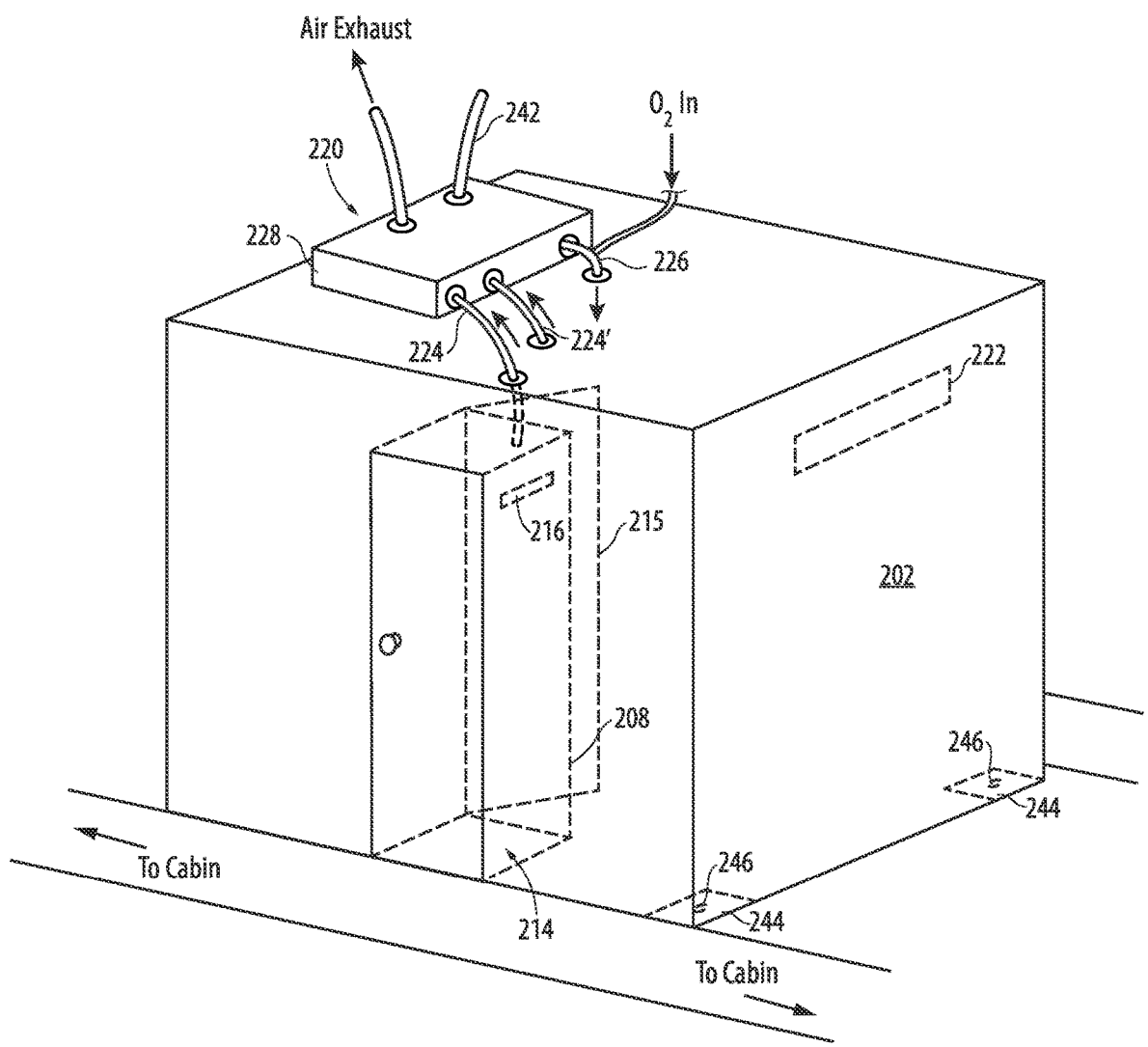
FIG. 3 is a schematic perspective view of another embodiment of an isolation section assembly constructed in accordance with the present disclosure, showing the section housing.
Figure 4:
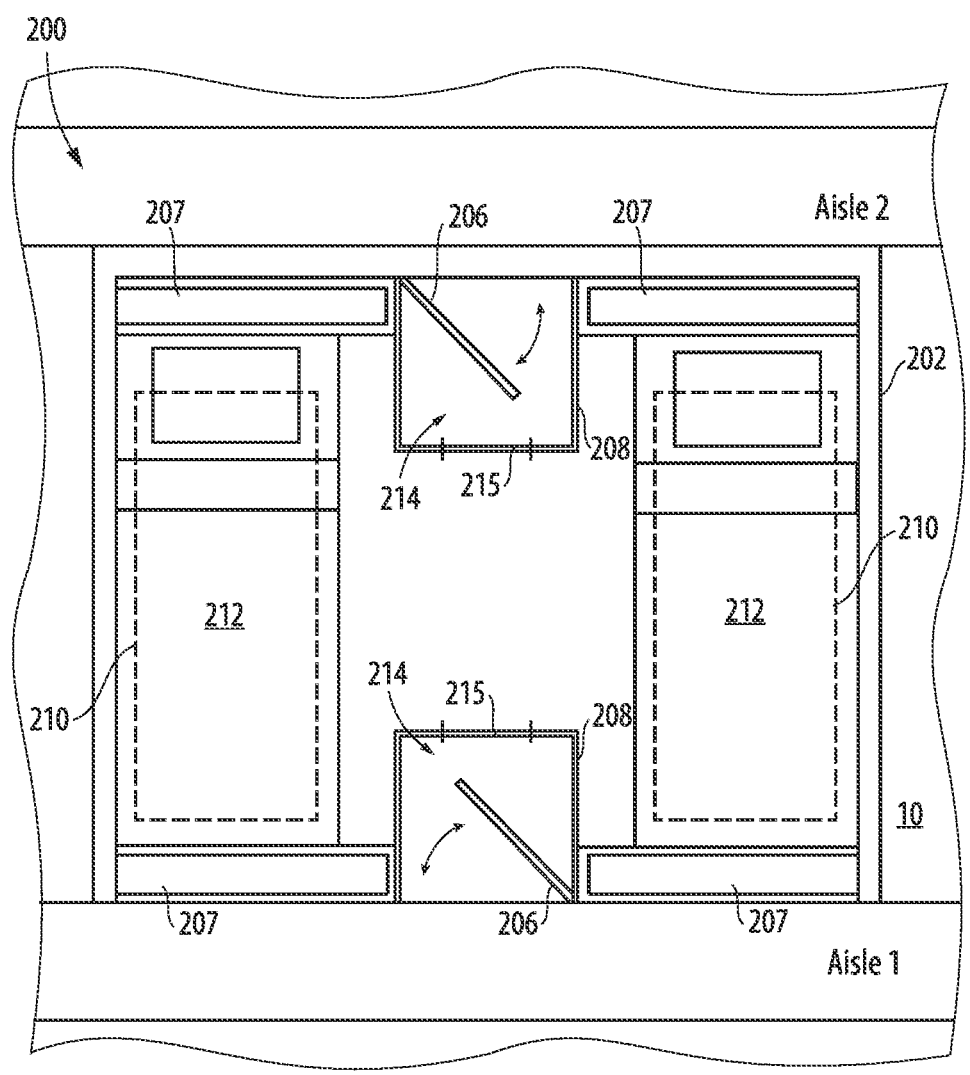
FIG. 4 is a schematic plan view of the isolation section assembly of FIG. 3, showing the interior space of the section housing, two interior airlock spaces and two doors.

With reference now to FIGS. 3-4, another embodiment of an isolation section assembly 200, or "pod," includes a section housing 202 defining an interior space 204 isolated from a cabin area 10, e.g. an aircraft cabin. Similar to assembly 100, the walls of the section housing 202 form a complete, isolated enclosure from the rest of the cabin area 10. Assembly 200 includes a first and second doors 206 with access to interior space 204. Assembly 200 is configured and adapted to replace a 2 or 3 door galley complex in a central position in the aircraft cabin on a twin aisle aircraft or any suitable location on other forms of mass transit transport. Assembly 200 includes first and second airlock enclosures 208. The isolation section assembly 200 is similar to assembly 100 except for the size, number of openings into an interior space 204 of section assembly 200, e.g., the second door 206 and second airlock enclosure 208, and the position of the airlock enclosures 208 relative to the housing 202. Both the first and second airlock enclosures 208 define respective second interior airlock spaces 214. First and second interior airlock spaces 214 are configured and adapted to be at a negative pressure relative to a cabin area and are otherwise the same as interior airlock space 114 except that instead of being outside of walls defining housing 202, interior airlock space 214 is positioned inside of housing 202. Airlock enclosures 208 each include a respective access door 215 to allow passage from the cabin area 10 into the airlock space 214 while the doors 206 into interior space 204 are closed. The first and second doors 206 are opposite from one another across the interior space 214. The interior space of the section housing includes a waste stowage system 207. The section housing 202 is constructed in the same manner as housing 102.

As shown in FIGS. 3 and 4, the interior space 204 of the section housing 202 includes beds 212 and a medical supply storage area 210, which is the same as medical supply storage area 110 except area 210 can be positioned underneath the beds 212. A bunk lift system could be an option to allow 2 or 3 bunks to be placed one above the other if required. The section 202 is configured and adapted to provide isolation for sick patients while also accommodating access for an attendant, similar to section 102. The section housing 202 includes a FAR-UV illumination system 222 positioned within the interior space 204, similar to system 122. Interior airlock space 214 includes a constant FAR-UVC illumination systems 216, similar to system 116, except that systems 216 are mounted to a wall of their respective airlock enclosures 208.

As shown in FIGS. 3 and 4, an air recirculation system 220 is in fluid communication with the interior space 204 of the section housing 202 and the interior airlock space 214 in the same manner as air recirculation system 120. The air recirculation system 220 includes inlet conduits 224 and 224' and a return conduit 226. An environmental conditioner 228 is positioned between the inlet conduits 224 and 224' and return conduit 226. The air recirculation system 220, its conduits, and environmental conditioner 228 are the same as air recirculation system 120 and environmental conditioner 128. The isolation section assembly 200 includes a communications and electrical interface input 242, which is the same as communications and electrical interface input 142. The isolation section assembly 200 includes connection points 244 operatively connected to the section housing 202. The connection points 244 are configured and adapted to couple to existing monument connection points 246 in aircraft cabin area 10, as described above in the embodiment of FIG. 1.

Figure 5:
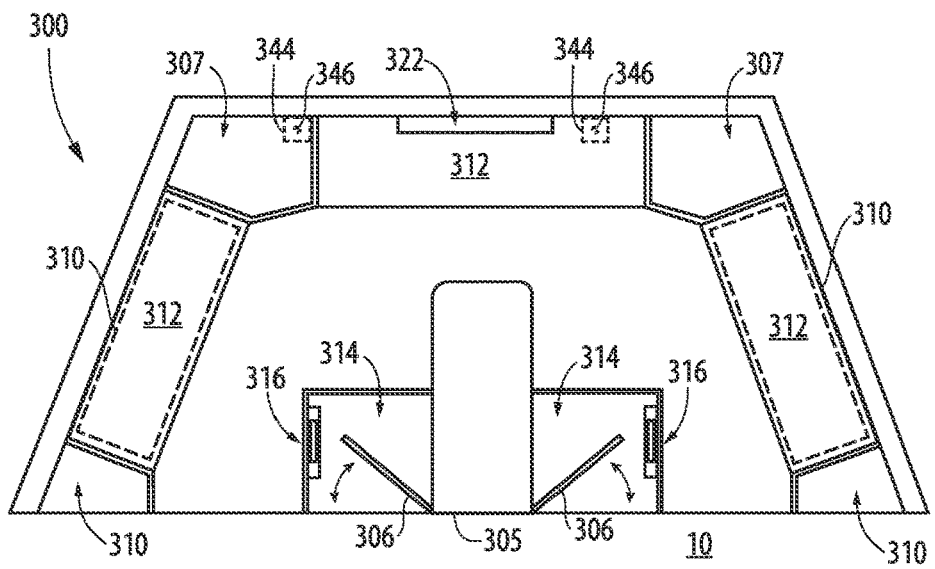
FIG. 5 is a schematic plan view of another embodiment of an isolation section assembly constructed in accordance with the present disclosure, showing two interior airlock spaces and two doors.

As shown in FIG. 5, another embodiment of an isolation section assembly 300, or "pod," includes a section housing 302 defining an interior space 304 isolated from a cabin area 10, e.g. an aircraft cabin. Isolation section assembly 300 is configured and adapted to replace an aft galley complex on single or twin aisle aircraft or any suitable location on other forms of mass transit transport, includes first and second doors 306 with access to interior space 304. Isolation section assembly 300 is generally the same as assembly 200 except that second door 306 is mounted on a common wall 305 of the section 302 with the first door 306. Similar to assembly 100, the walls of the section housing 302 form a complete, isolated enclosure from the rest of the cabin area 10. Assembly 300 includes first and second airlock enclosures 308. The isolation section assembly 300 is similar to assembly 200 except for the position of the airlock enclosures 308 and the doors 306. Both the first and second airlock enclosures 308 define respective interior airlock spaces 314, similar to spaces 214. First and second interior airlock spaces 314 are configured and adapted to be at a negative pressure relative to a cabin area 10 and are otherwise the same as interior airlock spaces 214. Airlock enclosure 308 includes an access door 315 to allow passage from the cabin area 10 into the airlock space 314 while the door 306 into interior space 304 is closed. The interior space of the section housing includes a waste stowage system 307. The section housing 302 is constructed in the same manner as housing 102.

With reference now to FIG. 5, the interior space 304 of the section housing 202 includes beds 312 and a medical supply storage area 310, which is the same as medical supply storage area 110 except area 310 can be positioned underneath the beds 312 or on the side. A bunk lift system could be an option to allow 2 or 3 bunks to be placed one above the other if required. The section 302 is configured and adapted to provide isolation for sick patients while also accommodating access for an attendant, similar to section 102. The section housing 302 includes a FAR-UV illumination system 322 positioned within the interior space 304, similar to system 122. Interior airlock space 314 includes a constant FAR-UVC illumination systems 316, similar to system 216. In some embodiments, assembly 300 can include an air recirculation system, similar to that of air recirculation system 120. It is also contemplated that, in some embodiments, assembly 300 can also include an environmental conditioner, similar to environmental conditioner 128. It is also contemplated that, in some embodiments, assembly 300 can also include a communications and electrical interface input, similar to input 142, which is the same as communications and electrical interface input 142. The isolation section assembly 300 includes connection points 344 operatively connected to the section housing 302. The connection points 344 are configured and adapted to couple to existing monument connection points 346 in aircraft cabin area 10, as described above in the embodiment of FIG. 1.

Figure 6:
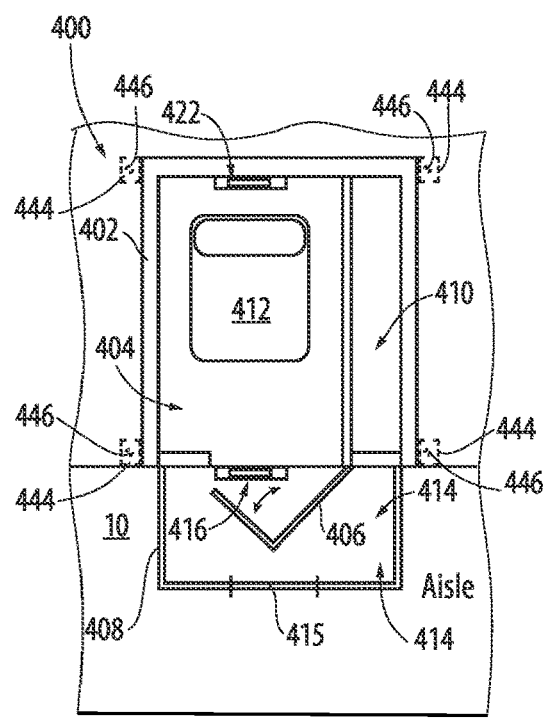
FIG. 6 is a schematic plan view of another embodiment of an isolation section assembly constructed in accordance with the present disclosure, showing the interior space of the section housing having a semi-reclining seat.

As shown in FIG. 6, another embodiment of an isolation section assembly 400, or "pod," includes a section housing 402 defining an interior space 404 isolated from a cabin area 10, e.g. an aircraft cabin. Assembly 400 is configured and adapted to replace a lavatory monument on single or twin aisle aircraft or any suitable location on other forms of mass transit transport. Isolation section assembly 400 includes a reclining chair 412 instead of a full bunk. The chair 412 could be fully or partially reclining. Isolation section assembly 400 is similar to assembly 100, with the primary difference being that section assembly 400 includes a reclining chair 412 instead of a bunk 112. Similar to assembly 100, the walls of the section housing 402 form a complete, isolated enclosure from the rest of the cabin area 10. Assembly 400 includes an airlock enclosure 408, similar to airlock enclosure 108. The airlock enclosure 408 defines an interior airlock space 414, similar to space 114. Interior airlock space 414 is configured and adapted to be at a negative pressure relative to a cabin area 10.

With continued reference to FIG. 6, the interior space 404 of the section housing 402 includes a medical supply storage area 410, which is the same as medical supply storage area 110. The section 402 is configured and adapted to provide isolation for sick patients while also accommodating access for an attendant, similar to section 102. The section housing 402 includes a FAR-UV illumination system 422 positioned within the interior space 404, similar to system 122. Interior airlock space 414 includes a constant FAR-UVC illumination systems 416, similar to system 116. In some embodiments, assembly 400 can also include an air recirculation system, similar to that of air recirculation system 120. It is also contemplated that in some embodiments, assembly 400 can also include an environmental conditioner, similar to conditioner 128, and/or a communications and electrical interface input, which could be the same as communications and electrical interface input 142. The isolation section assembly 400 includes connection points 444 operatively connected to the section housing 402. The connection points 444 are configured and adapted to couple to existing monument connection points 446 in aircraft cabin area 10, in a manner similar to that described above in the embodiment of FIG. 1.

A method for retrofitting an aircraft with an aircraft isolation assembly, e.g., assembly 100, 200, 300 or 400, includes mounting a section housing, e.g. section housing 102, 202, 302 or 402, to existing cabin monument connection points in a passenger cabin, e.g. aircraft cabin 10. The method includes coupling an airlock enclosure, e.g. airlock enclosure 108, 208, 308 or 408, to a door, e.g. door 106, 206, 306 or 406, of the section housing. The method includes fluidly coupling an air circulation system, e.g. air circulation system 120 or 220, to at least one of an existing cabin air exhaust or an existing $O_2$ source. The method includes electrically connecting a communications and electrical interface input, e.g. aircraft communications and electrical interface input 142 or 242, on the section housing to at least one of an existing aircraft communications system or an existing aircraft power source.

Embodiments of systems and methods described herein may result in increased passenger confidence in travel safety, helping to encourage mass travel again post-pandemic. The methods and systems of the present disclosure, as described above and shown in the drawings, provide for a system to safely and effectively allow for ill passengers to travel. While the apparatus and methods of the subject disclosure have been shown and described, those skilled in the art will readily appreciate that changes and/or modifications may be made thereto without departing from the scope of the subject disclosure.

What is claimed is:

1. An aircraft comprising, an isolation section assembly further comprising:
    a section housing, connected to at least one monument connection point within the aircraft cabin, defining an interior space, the section housing including at least one door with access to the interior space;
    an airlock enclosure positioned within an aircraft aisle, the airlock enclosure abutting the door and comprising a first aisle door and a second aisle door each providing access from a cabin area to the airlock enclosure, the airlock enclosure defining an interior airlock space, wherein the interior airlock space is configured and adapted to be at a negative pressure relative to the cabin area; and
    an air recirculation system in fluid communication with at least one of the interior space of the section housing or the interior airlock space.

2. The isolation section assembly as recited in claim 1, wherein the section housing includes a UV illumination system positioned within the interior space configured and adapted to disinfect the interior space.

3. The isolation section assembly as recited in claim 1, wherein the air recirculation system includes an inlet conduit and a return conduit, and an environmental conditioner therebetween.

4. The isolation section assembly as recited in claim 3, wherein the environmental conditioner includes at least one of a carbon filter, an ozone scrubber, a UVC light or a chemical sanitizer.

5. The isolation section assembly as recited in claim 3, wherein the return conduit is in fluid communication with an $O_2$ source to receive $O_2$ therefrom.

6. The isolation section assembly as recited in claim 3, wherein the return conduit fluidly connects an outlet of the environmental conditioner and the interior space of the section housing.

7. The isolation section assembly as recited in claim 1, wherein the interior space of the section housing includes at least one bunk bed, at least one reclining chair, or both.

8. The isolation section assembly as recited in claim 1, wherein the interior space of the section housing includes a waste stowage system.

9. The isolation section assembly as recited in claim 1, wherein the interior space of the section housing includes a medical supply storage area.

10. The isolation section assembly as recited in claim 1, further comprising a second door with access to the interior space and a second airlock enclosure abutting the second door, the second airlock enclosure defining a second interior airlock space, wherein the second interior airlock space is configured and adapted to be at a negative pressure relative to a cabin area.

11. The isolation section assembly as recited in claim 10, wherein the door is a first door, wherein the second door is opposite from the first door across the interior space.

12. The isolation section assembly as recited in claim 10, wherein the door is a first door, wherein the second door is mounted on a common wall with the first door.

13. The isolation section assembly as recited in claim 1, further comprising a communications and electrical interface input operatively connected to the section housing.

* * * * *